(12) United States Patent
Nakamura et al.

(10) Patent No.: US 6,465,512 B2
(45) Date of Patent: Oct. 15, 2002

(54) LEUKEMIC CELL GROWTH INHIBITING METHOD

(75) Inventors: Osamu Nakamura, Tosu (JP); Yoko Fuke, Kodaira (JP); Hideki Ohba, Kitakyushu (JP); Seiji Yasuda, Tosu (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 27 days.

(21) Appl. No.: 09/733,947

(22) Filed: Dec. 12, 2000

(65) Prior Publication Data

US 2002/0022655 A1 Feb. 21, 2002

(30) Foreign Application Priority Data

Dec. 13, 1999 (JP) ............................................ 11-353084

(51) Int. Cl.⁷ ................................................. A61K 31/26
(52) U.S. Cl. .......................... 514/514; 514/885; 514/908
(58) Field of Search ................................. 514/514, 885, 514/908

(56) References Cited

U.S. PATENT DOCUMENTS 5,411,986 A * 5/1995 Cho et al. .................... 514/514
6,008,260 A * 12/1999 Pezzuto et al. ............. 514/733

OTHER PUBLICATIONS

Zhang et al., Proc. Natl. Acad. Sci., USA, vol. 89, pp. 2399–2403 (1992).

Zhang et al., Proc. Natl. Acad. Sci., USA, vol. 91, pp. 3147–3150 (1994).

Chen et al., The Journal of Biological Chemistry, vol. 273, No. 3, pp. 1769–1775 (1998).

* cited by examiner

Primary Examiner—Frederick Krass
(74) Attorney, Agent, or Firm—Wenderoth, Lind, & Ponack, L.L.P.

(57) ABSTRACT

Disclosed is a method for growth inhibition of human leukemic cells or therapeutic treatment method of a leukemic patient by using a medicament of which the effective ingredient is a methylsulfinylalkyl isothiocyanate such as 4-(methylsulfinyl)butyl isothiocyanate and 6-(methylsulfinyl)hexyl isothiocyanate, which can be prepared by extraction from the tissues of certain plants and can induce apoptosis in human leukemic cells. This medicament compound is little growth-inhibitive against normal cells as compared with leukemic cells, so that a remarkable therapeutic effect can be expected.

8 Claims, 5 Drawing Sheets

LEUKEMIC CELL GROWTH INHIBITING METHOD

BACKGROUND OF THE INVENTION

The present invention relates to a novel leukemic cell growth inhibiting agent or, more particularly, to a leukemic cell growth inhibiting method by using a medicament of which the effective ingredient is a methylsulfinylalkyl isothiocyanate derived from certain plants belonging to the family of Cruciferae. The invention further relates to a therapeutic method for leukemia.

As is known, leukemia is a disease caused by the autonomic growth of leukocytes in the bone marrow and sometimes called a blood cancer accompanied by anemia, leukocytosis, thrombocytopenia and the like. In addition, it is known that leukemia sometimes leads to formation of secondary infiltration focuses, i.e. metastasis, or secondary hematopoietic focuses in other organs such as the liver, spleen, lymph nodes and the like.

A great variety of compounds are proposed as a therapeutic medicament of leukemia including synthetically prepared compounds, antibiotics and natural substances as well as interferons, interleukins, TNFs (tumor necrosis factors), CSF- (colony-stimulating factors) suppressing substances and the like as bio-technological products. These medicaments have an activity of interacting with the leukemic cells to inhibit growth thereof or to cause necrosis thereof so as to exhibit a therapeutic effect on the leukemia. Necrosis mentioned above to kill cells involves very serious defects that the cell-killing effect extends not only to the diseased cells but also to normal cells therearound and other new diseases are resulted.

Accordingly, it is eagerly desired to develop a novel therapeutic medicament for leukemia which never affects any normal cells acting only on the diseased cells to cause growth inhibition or necrosis thereof.

Several apoptosis-inducing leukemic cell growth inhibitors were discovered as a therapeutic medicament for leukemia satisfying the above mentioned requirements including lectin proteins extracted from the pulpous flesh of a fungus called yanagimatsutake (*Agrocybe cylindracea*), lectin proteins separated from the beans of touazuki (*Abrus precatorius*), hinokitiol extracted from the plants belonging to the family of cypresses and others.

The apoptosis mentioned above is a life phenomenon to avoid the disadvantage caused by persistence of damaged cells which can be repaired with great difficulties, in which such damaged cells are autolytically destroyed along a sequence of programs. Namely, a therapeutic medical means for leukemia could be provided by using such an apoptosis-inducing leukemic cell growth inhibitor since the leukemic cells in the blood alone can be selectively destroyed by autolysis with little influences on normal cells.

It is known that, when the tissue of a plant belonging to the family of Cruciferae is ground, a methylsulfinylalkyl isothiocyanate is formed from the glucosinolate in the tissue. As is reported, some of these isothiocyanate compounds exhibit a suppressing effect against esophageal cancer and proventriculus cancer of rats artificially induced by nitrosamine and the gastric cancer, mammary cancer and lung cancer of human suspectedly induced by 7,12-dimethylbenz[a]anthracene or benzo[a]pyrene but no information is available on the activity of these isothiocyanate compounds against leukemic cells.

SUMMARY OF THE INVENTION

The present invention accordingly has an object to provide a novel therapeutic method for growth inhibition of leukemic cells by administrating the leukemic patient with a novel apoptosis-inducing leukemic cell growth inhibitor which is a compound obtained from a raw material of good availability.

Thus, the growth inhibiting method against leukemic cells provided by the present invention comprises: bringing the leukemic cells into contact with a leukemic cell growth inhibitor which is a methylsulfinylalkyl isothiocyanate represented by the general formula

$$CH_3-SO-(CH_2)_n-N=C=S, \quad (I)$$

in which the subscript n is a positive integer in the range from 2 to 8.

DETAILED DESCRIPTION OF THE PREFERRED EMBODIMENTS

Figure 1:
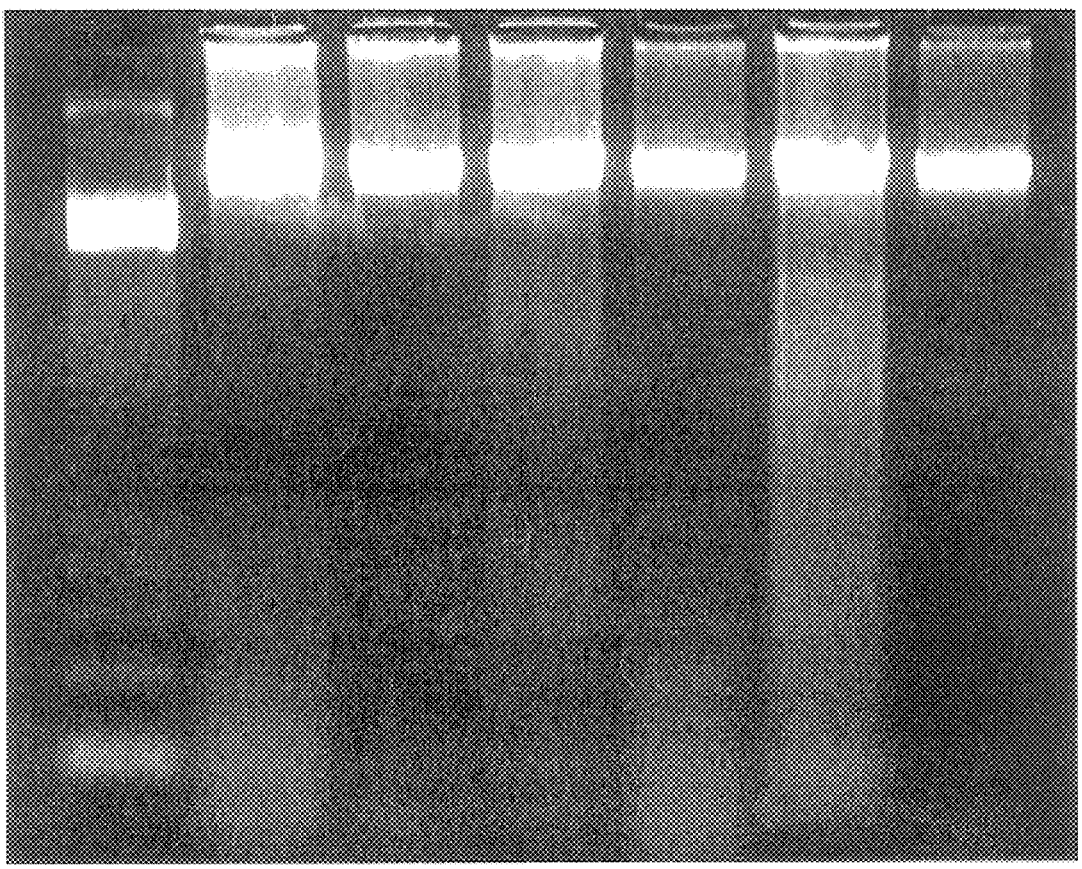
FIG. 1 is a photograph showing the state of the DNA segments obtained from Jurkat cells after treatment with 4-(methylsulfinyl)butyl isothiocyanate or with 6-(methylsulfinyl)hexyl isothiocyanate.

Although the methylsulfinylalkyl isothiocyanate compound represented by the general formula (I), which is the effective ingredient with which leukemic cells are brought into contact for the purpose of growth inhibition, can be prepared by a chemical synthetic method known per se, it is preferable from the standpoint of cost saving and utilization of natural resources that the compound is obtained by extraction from the tissues of certain plants belonging to the family of Cruciferae such as *Wasabi japonica* Matsum., i.e. sawawasabi, and *Brassica oleracea italica*, i.e. broccoli. The isothiocyanate compound can be extracted from the tissues of these plants in the following manner. Thus, the plant tissues sliced into small pieces are admixed with ethyl ether and kept standing for 24 hours. The extract by ethyl ether is paper-filtrated and dehydrated by adding sodium sulfate anhydrous, and, then, ethyl ether is vapored off.

In the next place, the dried material is dissolved in methyl alcohol, and subjected to gel filtration according to a known procedure, and, if necessary, to fractionation of the active fractions by high-performance liquid chromatography followed by freeze-drying.

The tissues of broccoli give a mixture of methylsulfinylalkyl isothiocyanates mainly consisting of 4-(methylsulfinyl)butyl isothiocyanate, while a mixture of methylsulfinylalkyl isothiocyanates mainly consisting of 6-(methylsulfinyl)hexyl isothiocyanate is obtained from the tissues of sawawasabi.

The synthetic method for the preparation of a methylsulfinylalkyl isothiocyanate compound is described, for example, in Proceedings of National Academy of Science, U.S.A., volume 89, page 2399, according to which the compound is obtained by the oxidation reaction of a compound represented by the general formula

$$CH_3\text{—}S\text{—}(CH_2)_n\text{—}N\text{=}C\text{=}S, \quad (II)$$

in which the subscript n has the same meaning as in the general formula (I), with an oxidizing agent such as nitric acid and hydrogen peroxide.

Following procedures are effective for the assay of methylsulfinylalkyl isothiocyanate obtained by the methods described above to inhibit the growth activity of human leukemic cells by apoptosis. Thus, when the effect of isothiocyanate is observed, a fluorescent dye like propidium iodide is added to the culture to monitor the state of nuclei by laser confocal microscopy. The nuclear fragmentation is a unique characteristic for apoptosis. In the earlier stage of apoptosis, the enzyme caspases activation, translocation of phosphatidylserine in plasma membrane, and mitochondrial transmembrane potential decrease can be good markers to be observed.

The therapeutic treatment of a leukemic patient according to the inventive method is undertaken by parenterally administrating the patient with the leukemic cell growth inhibitor. Though dependent on the diseased condition of the patient, the administration dose of the leukemic cell growth inhibitor is usually in the range from 0.01 to 10 mg/kg body weight per day. Since the medicament exhibits the leukemic cell growth inhibition by the mechanism of apoptosis induction, the effective dose can be much smaller than the administration dose of other known cell growth inhibitors. The medicament form of the cell growth inhibitor is preferably an aqueous solution of 0.1 to 10% by weight concentration with optional admixture of various additives conventionally added to an injection fluid such as solubilizers, buffer agents, isotonic agents, stabilizers, preservatives, indolence agents and the like.

In the following, Examples are given to illustrate the present invention in more detail.

EXAMPLE 1

T-cell series Jurkat cells originated from a patient of acute lymphatic leukemia were cultured in RPM1-1640 culture medium supplemented with 10% of fetal calf serum, 1% of glutamine, and 100 µg/ml of streptomycin and 100 units/ml of penicillin as antibiotics under a humidified atmosphere of 5% carbon dioxide at 37° C. to give an established cell strain.

A 96-well microwell plate was inoculated with 90 µl of $2.22\times10^5$ cells/ml culture fluid obtained above and 10 µl of 15.6 µg/ml solution of 4-(methylsulfinyl)butyl isothiocyanate or 6-(methylsulfinyl)hexyl isothiocyanate was added 24 hours later. After standing for 20 hours, the cells were recovered from the microwell plate and subjected to the extraction of DNA. In the next place, the extracted DNA was subjected to electrophoresis on 1.5% Agarose gel and stained with ethidium bromide to observe fragment formation by the irradiation with ultraviolet light. The results are shown in FIG. 1.

Lanes 1 to 7 of FIG. 1 show: the ladder marker (lane 1); control (lane 2); control with addition of caspases inhibitor in a concentration of 100 µM (lane 3); 4-(methylsulfinyl) butyl isothiocyanate (lane 4); 4-(methylsulfinyl)butyl isothiocyanate with addition of caspases inhibitor in a concentration of 100 µM (lane 5); 6-(methylsulfinyl)hexyl isothiocyanate (lane 6); and 6-(methylsulfinyl)hexyl isothiocyanate with addition of caspases inhibitor in a concentration of 100 µM (lane 7), respectively. The caspases inhibitor employed here is carbobenzoxy-Asp-$CH_2$-dichlorobenzoyloxy methane.

EXAMPLE 2

The culture fluid containing $2.22\times10^5$ cells/ml of the established cell strain obtained in Example 1 was cultured in the volume of 90 µl for 24 hours under the same conditions as in Example 1, and the culture received 10 µl of phosphate buffered saline containing 4-(methylsulfinyl)butyl isothiocyanate in the concentrations of the range of 1 to 50 µg/ml followed by further 20 hours of incubation at 37° C. under a humidified atmosphere of 5% carbon dioxide.

The cells in each 100 µl of the culture incubated with 4-(methylsulfinyl)butyl isothiocyanate were subjected to the determination of the activity of mitochondrial dehydrogenase using a tetrazolium salt and the results were employed to show the relationship between the cell survival rate and concentration of 4-(methylsulfinyl)butyl isothiocyanate.

Figure 2:
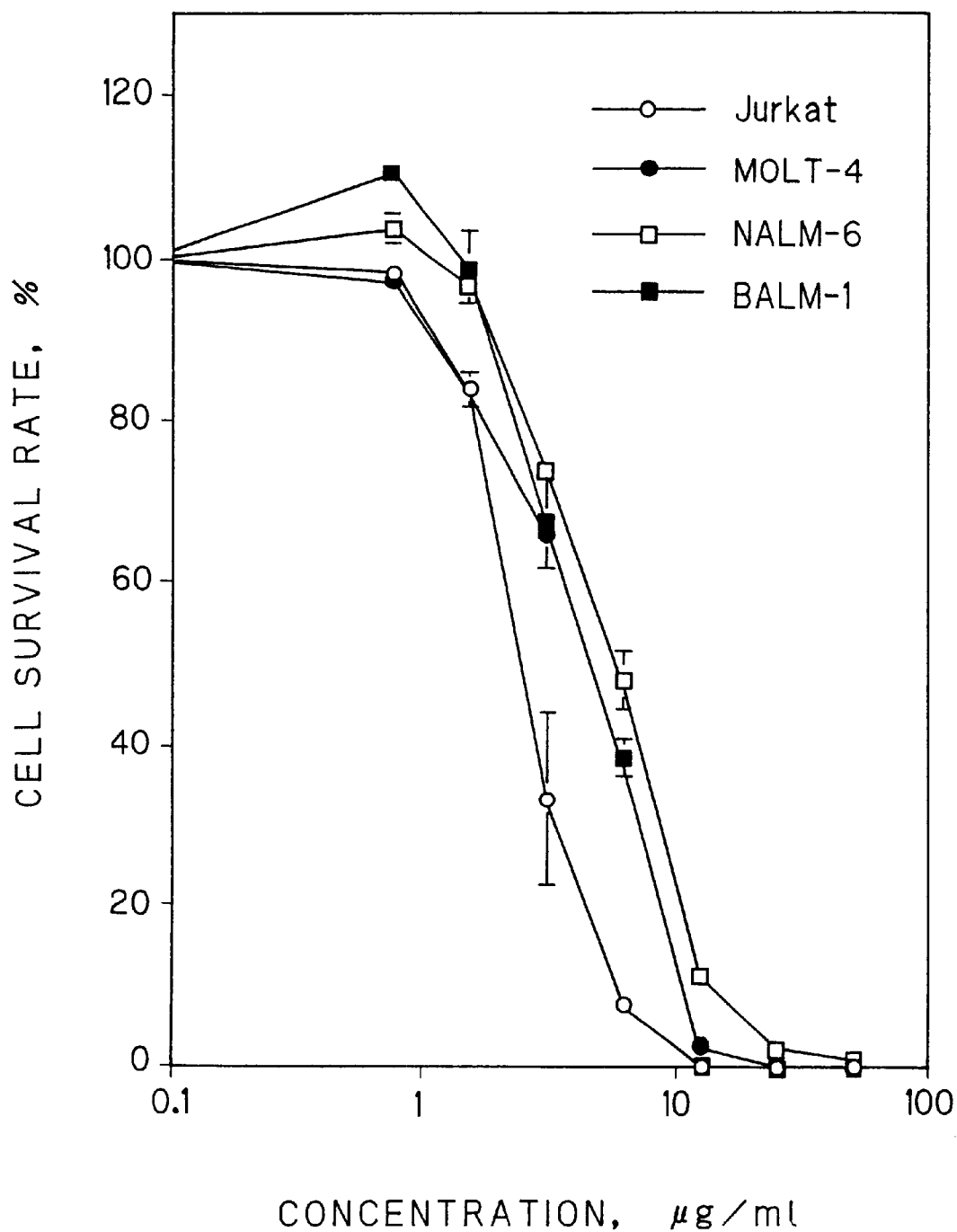
FIG. 2 is a graph showing the cell survival rates of different strains of leukemic cells as a function of the concentration of 4-(methylsulfinyl)butyl isothiocyanate.

FIG. 2 is a graph showing the cell survival rates as a function of the concentration of 4-(methylsulfinyl)butyl isothiocyanate.

In the next place, the same assay procedure as above was repeated with replacing Jurkat cells originated from acute lymphoblastic leukemia with T-cell series MOLT-4 cells originated from acute lymphoblastic leukemia, B-cell series NALM-6 cells originated from acute lymphoblastic leukemia or the same B-cell series BALM-1 cells. FIG. 2 also shows the cell survival rates obtained in these assays as a function of the concentration of 4-(methylsulfinyl)butyl isothiocyanate.

EXAMPLE 3

The experimental procedures were substantially the same as in Example 2 except that 6-(methylsulfinyl)hexyl isothiocyanate extracted from sawawasabi was employed instead of 4-(methylsulfinyl)butyl isothiocyanate.

Figure 3:
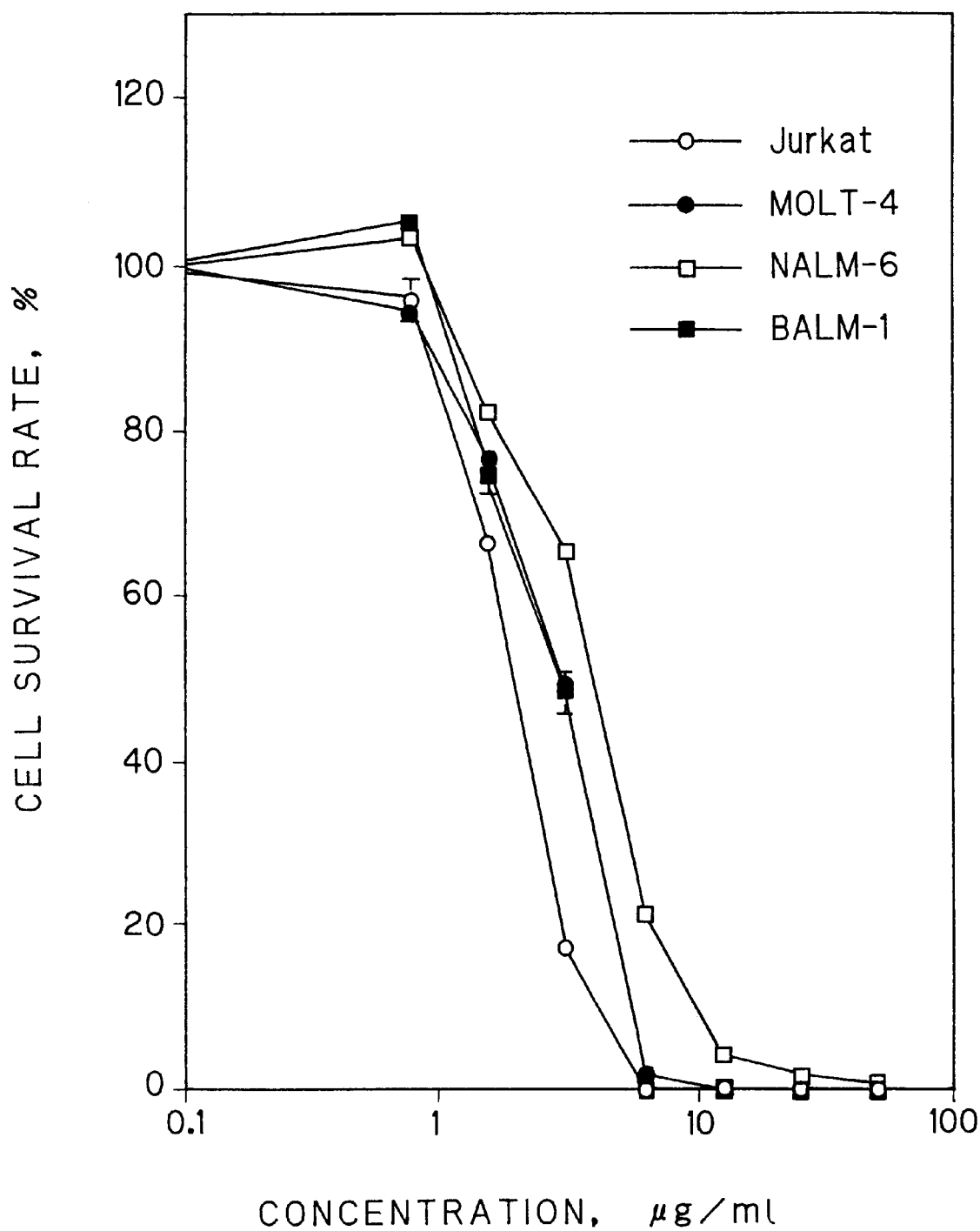
FIG. 3 is a graph showing the cell survival rates of different strains of leukemic cells as a function of the concentration of 6-(methylsulfinyl)hexyl isothiocyanate.

FIG. 3 is a graph showing the cell survival rates as a function of the concentration of 6-(methylsulfinyl)hexyl isothiocyanate.

Reference Example 1

The experimental procedures were substantially the same as in Example 2 except that normal-O cells, normal-A cells or normal-B cells derived from normal lymphocytes of three healthy persons were assayed instead of Jurkat cells.

Figure 4:
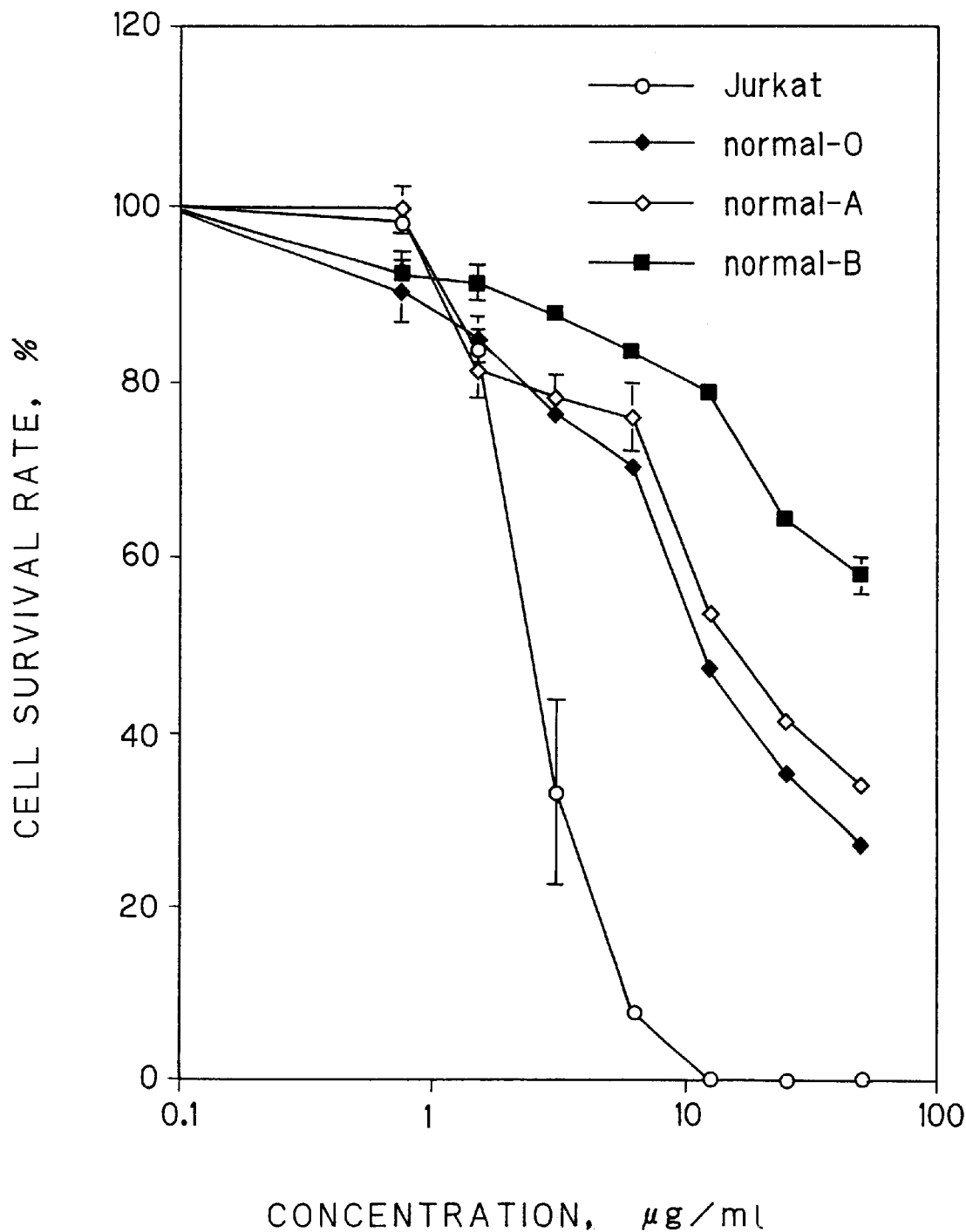
FIG. 4 is a graph showing the cell survival rates of different lymphocytes derived from three healthy persons and Jurkat cells as a function of the concentration of 4-(methylsulfinyl)butyl isothiocyanate.

FIG. 4 is a graph showing the cell survival rates as a function of the concentration of 4-(methylsulfinyl)butyl isothiocyanate. The figure also includes the results obtained with Jurkat cells for comparison.

Reference Example 2

The experimental procedures were substantially the same as in Example 3 except that normal-O cells, normal-A cells or normal-B cells derived from normal lymphocyte cells of three healthy persons were assayed instead of Jurkat cells.

Figure 5:
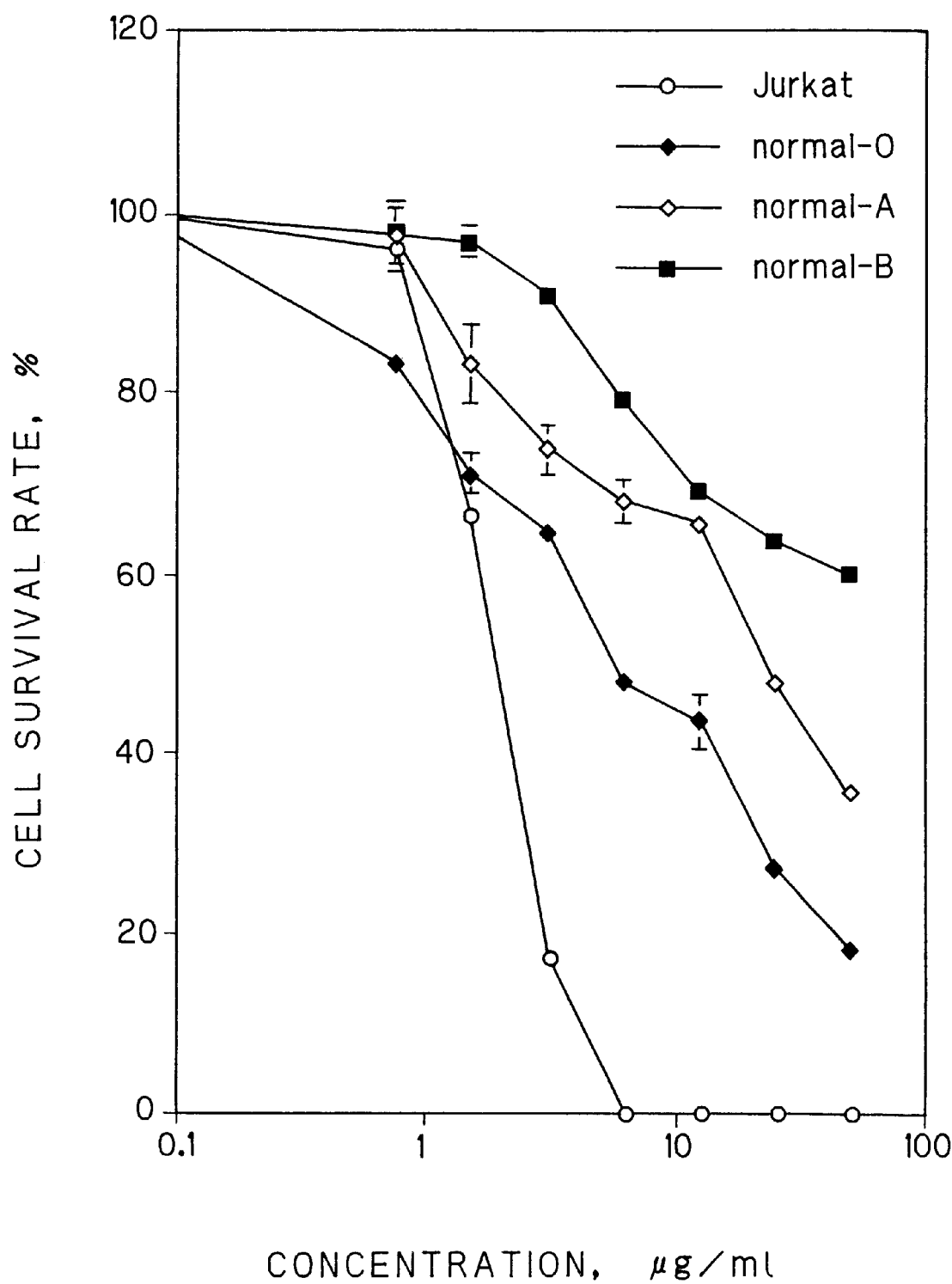
FIG. 5 is a graph showing the cell survival rates of different lymphocytes derived from three healthy persons and Jurkat cells as a function of the concentration of 6-(methylsulfinyl)hexyl isothiocyanate.

FIG. 5 is a graph showing the cell survival rates as a function of the concentration of 6-(methylsulfinyl)hexyl isothiocyanate. The figure also includes the results obtained with Jurkat cells for comparison.

As is clear from comparison of FIGS. 2 to 5, the cytotoxicity of the leukemic cell growth inhibitor used in the inventive method against normal lymphocyte cells is much lower than against leukemic cells, so that the inventive method could provide a very potential therapeutic means for leukemia.

What is claimed is:

1. A method for growth inhibition against leukemic cells which comprises:

bringing the leukemic cells into contact with a leukemic cell growth inhibitor which is a methylsulfinylalkyl isothiocyanate represented by the general formula $$CH_3-SO-(CH_2)_n-N=C=S,$$

in which the subscript n is a positive integer in the range from 2 to 8.

2. The method for growth inhibition against leukemic cells as claimed in claim 1 in which the leukemic cell growth inhibitor is 4-(methylsulfinyl)butyl isothiocyanate.

3. The method for growth inhibition against leukemic cells as claimed in claim 1 in which the leukemic cell growth inhibitor is 6-(methylsulfinyl)hexyl isothiocyanate.

4. A therapeutic treatment method of a leukemic patient which comprises administrating the patient with a leukemic cell growth inhibitor which is a methylsulfinylalkyl isothiocyanate represented by the general formula $$CH_3-SO-(CH_2)_n-N=C=S,$$

in which the subscript n is a positive integer in the range from 2 to 8.

5. The therapeutic treatment method of a leukemic patient as claimed in claim 4 in which the administration of the patient with the leukemic cell growth inhibitor is conducted parenterally.

6. The therapeutic treatment method of a leukemic patient as claimed in claim 4 in which the administration dose of the patient with the leukemic cell growth inhibitor is in the range from 0.01 to 10 mg/kg body weight per day.

7. The therapeutic treatment method of a leukemic patient as claimed in claim 4 in which the leukemic cell growth inhibitor is 4-(methylsulfinyl)butyl isothiocyanate.

8. The therapeutic treatment method of a leukemic patient as claimed in claim 4 in which the leukemic cell growth inhibitor is 6-(methylsulfinyl)hexyl isothiocyanate.

* * * * *